United States Patent [19]

Rios

[11] Patent Number: 4,652,116
[45] Date of Patent: Mar. 24, 1987

[54] FINGERPRINT RECORDING METHOD AND APPARATUS

[76] Inventor: Arturo M. Rios, P.O. Box 10069, St. Peterburg, Fla. 33733

[21] Appl. No.: 825,895

[22] Filed: Feb. 4, 1986

Related U.S. Application Data

[63] Continuation-in-part of Ser. No. 465,811, Apr. 17, 1984, Pat. No. 4,568,178.

[51] Int. Cl.$^4$ .................... G03B 27/52; G03B 27/32; G03B 29/00
[52] U.S. Cl. ........................................ 355/40; 354/62; 355/77
[58] Field of Search ................ 355/40, 47, 49, 77; 354/62, 109

[56] References Cited

U.S. PATENT DOCUMENTS

| | | | |
|---|---|---|---|
| 3,529,520 | 9/1970 | Thiebault | 354/62 |
| 3,906,520 | 9/1975 | Phillips | 354/62 |
| 4,152,056 | 5/1979 | Fowler | 354/62 |
| 4,537,484 | 8/1985 | Fowler et al. | 354/62 |
| 4,568,178 | 2/1986 | Rios | 355/40 |

Primary Examiner—Richard A. Wintercorn
Attorney, Agent, or Firm—L. Lawton Rogers, III; Joseph M. Killeen

[57] ABSTRACT

The disclosed apparatus is an electro-optical fingerprint copier.

The apparatus uses a camera with one or more lenses to copy the impression made by the ridges on the tips of fingers and thumbs. These impressions are useful as a means for identification since no two persons have the same pattern of ridges.

The apparatus also includes an automatic chart feeder, positioning and releaser, an automatic shutter control and lense system to position fingers. The features make possible the processing of an accurate fingerprint chart in a very short time.

32 Claims, 9 Drawing Figures

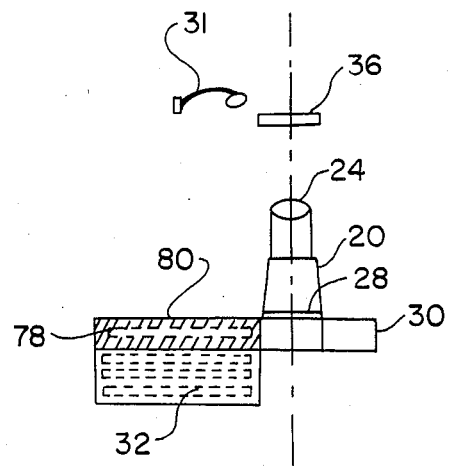
FIG. 4
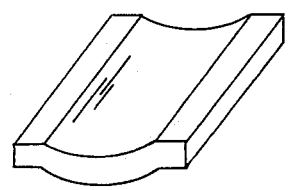
FIG. 5
FIG. 6

FINGERPRINT RECORDING METHOD AND APPARATUS

RELATED APPLICATIONS

This application is a continuation-in-part of application Ser. No. 465,811 filed Apr. 17, 1984, now issued as U.S. Pat. No. 4,568,178 issued Feb. 4, 1986.

BACKGROUND OF THE INVENTION

This invention relates to copiers and more particularly, to an electro-optical fingerprint photocopier to make accurate copies of the impressions of the fingerprints of a person.

A conventional procedure of fingerprinting for identification purposes utilizes ink, an ink pad, a roller and a chart to get an impression of the finger ridges. Typically each of the fingers of the fingerprinted person, in turn, are immersed in a wet ink and rolled across a flat white surface, usually paper, which receives and holds the fingerprint impression. This is a relatively slow and uncomfortable process in which both the operator and the fingerprinted person stain their hands with ink.

Additionally, the amount of ink applied to the fingers and transferred to the white surface is difficult to control. Inadequate or excessive inking frequently fails to record details of the fingerprints. Likewise, the amount of pressure applied to the fingers while making the impressions can cause smearing of the ink, inadequate ink transfers to the impression or distortion of the fingerprint. These difficulties and others require that the operator be both trained and experienced and repeated attempts to obtain a complete set of usable fingerprints are common.

There is thus a growing need for an accurate and easy-to-use fingerprint copier and recorder to improve and accelerate the fingerprinting procedure for identification purposes. Such an apparatus should have the capability of reducing the time to record the finger impressions.

It is therefore an object of the present invention to provide a fingerprint copier that accurately copies in color or black and white a fingerprint impression.

It is another object of the present invention to provide an electro-optical fingerprint copier that automatically positions a film chart during the fingerprinting process at the command of the operator thereby reducing the fingerprinting time.

It is still another object of the present invention to provide an electro-optical fingerprint copier that copies the fingerprint impressions on a film chart thereby eliminating the use of ink during fingerprinting.

It is a further object of the present invention to provide an electro-optical fingerprint copier that generates a fingerprint image into a flat image thereby making unnecessary to roll over the finger whose impressions are to be copied.

It is a further object of the present invention to provide an electro-optical fingerprint copier that reduces the fingerprinting time by copying more than one finger at the same time.

This invention accomplishes these and other objects by providing an electro-optical copier having an array of concave-convex lenses to position the fingers. On the concave cylindrical face of a concave-convex lens a finger is positioned so as to expose the fingerprint. The concave-convex lens generates a fingerprint flat image which image enters a macrolens camera and by means of an automatic shutter it is recorded on a flat film chart surface. This operation is repeated simultaneously for a number of fingers, in an automatic mode and at the command of the operator. Also in order to record fingerprint images at several intervals during the fingerprinting process, the film chart positions automatically so as to expose unused chart zones under the shutters about to open. A new film chart is automatically fed into the camera to start the process again. Plane lenses may be used for flat fingerprinting.

These features eliminate the need for inking the fingertips of a person, the need for the person to rotate its fingers during the fingerprinting process and the continuous handling of charts during the process. All these contribute to speed up the fingerprinting process saving operator time and reducing operator training requirements.

When the fingerprinting process ends, a ready-to-use film chart having the recorded fingerprint impressions is released from the apparatus. A significant advantage of this chart is that later it may be recopied by ordinary means.

Furthermore, this apparatus may be arranged as a small portable unit with the finger positioning lenses, the selector keys, the film chart feeder and the film chart releaser conveniently installed at different sides of the unit. In this way the handling activity of the operator will not interfere with the hand movements of the fingerprinted person. Also, the area surrounding the finger positioning lenses from impressions caused by finger contact. This cleaning operation occurs immediately after the fingerprinting of a person ends.

Other objects, features and advantages of the present invention will become apparent from the following detail description taken in conjunction with the accompanying drawings.

BRIEF DESCRIPTION OF THE DRAWINGS

FIG. 4 is a schematic diagram of a film chart used in the apparatus of FIG. 1 illustrating the recording zones of the chart;

FIG. 5 is a schematic side diagram of the apparatus of FIG. 1 illustrating the shutter assembly and the finger positioning assembly;

FIG. 6 is a perspective schematic diagram of a concave-convex lens of the apparatus of FIG. 1;

Figure 1:
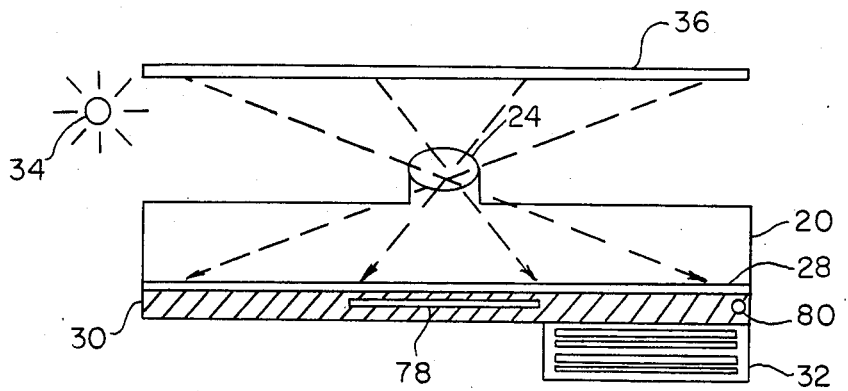
FIG. 1 is a schematic side diagram of the apparatus according to the invention.

DETAILED DESCRIPTION OF THE PREFERRED EMBODIMENT:

Referring to FIG. 1, reference numeral 20 denotes the interior camera of the apparatus; 24 denotes the lenses of the camera 20 of this embodiment; 28 denotes a shutter assembly; 30 denotes a film chamber; 32 denotes a chart feeder; 34 denotes a light source inside the apparatus; and 36 denotes a finger positioning assembly.

Figure 2:
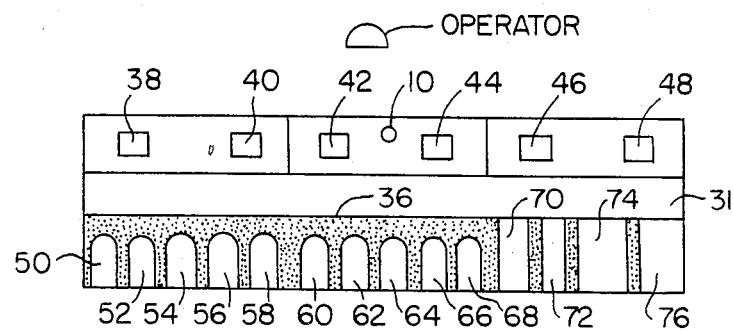
FIG. 2 is a schematic top diagram of the apparatus of FIG. 1 illustrating the selector keys and the finger positioning assembly.

In FIG. 2, reference numerals 38, 40, 42, 44, 46, and 48 denote illuminating selector keys; 50, 52, 54, 56, and 58 denote concave-convex lenses to position the thumb, index, middle, ring and little fingers of the right hand, respectively; 74 and 76 denote plane lenses to position the left four fingers and the right four fingers, respectively; and 10 denotes a red light indicator.

Figure 3:
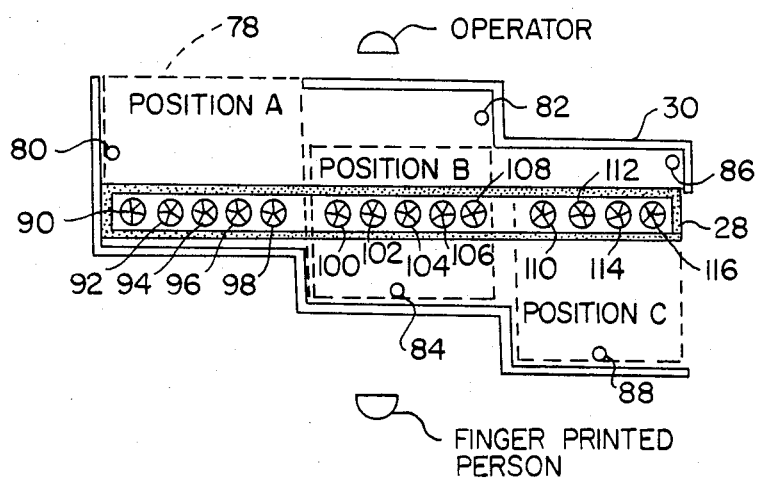
FIG. 3 is a schematic top section of the apparatus of FIG. 1 illustrating the shutter assembly, the film chamber and various positions of a film chart during the fingerprinting operation.

In FIG. 3, reference numeral 78 denotes a film chart; 80, 82, 84, 86, and 88 denote electronic sensors; 90, 92, 94, 96, 98, 100, 102, 104, 106, 108, 110, 112, 114, and 116 denote shutters in the shutter assembly 28.

In an embodiment of the present invention, the camera 20, shown in FIG. 1, receives fingerprint images from the lenses in the fingers positioning assembly 36. These images enter through lens 24. The fingers positioned on assembly 36 receive illumination from light source 34 located inside the system. The images are projected on the corresponding shutters in the shutter assembly 28. At the command of the operator the corresponding shutters open and the images enter the film chamber 30 to be recorded on the film chart 78, which is positioned properly inside chamber 30. After the last images are recorded on chart 78 it is released outside the system ready for use. Now a new film chart 78 is fed into chamber 30 from the film feeder assembly 32. If the film feeder assembly 32 is empty, the sensor 80 will activate the red light indicator 10 announcing to the operator that the apparatus needs another film chart pack.

In FIG. 4, the film chart 78 is divided in 14 zones. Reference numerals 118, 120, 122, 124, and 126 denote the zones to record fingerprint images pertaining to the thumb, and the little, ring, middle and index fingers of the left hand, respectively; 128, 130, 132, 134, and 136 denote the zones to record fingerprint images pertaining to the left and right thumb, respectively; and 142 and 144 denote the zones to record fingerprint images of the four fingers of the left and right hand, respectively.

The film chart 78 may be a conventional photographic film and preferably a self-developing film which yields a positive image. Alternatively the film chart 78 may be any medium onto which an image may be permanently stored, such as ordinary paper onto which a xerographic or lasergraphic image is place, heat or light sensitive treated paper, or microfilm. Additionally, the film chart 78 may be a analog or digital recording apparatus which records analog or digital signals corresponding to the image of the fingerprint.

Referring now to FIGS. 2, 3, and 4, the fingerprinted person positions his left thumb on lens 50 of the assembly 36. At this time the selector key 38 is the only one illuminated and the film chart 78 is in position A on chamber 30. When the operator pushes selector key 38, shutter 98 opens and the image of the left thumb is recorder on zone 118 of the film chart 78. Selector key 38 turns off and selector key 40 now illuminates. Afterward, the person positions the four fingers of his left hand on lenses 52, 54, 56, and 58. At this particular time, the film chart is still in position A on chamber 30. When the operator pushes selector key 40, the shutters 96, 94, 92, and 90 open simultaneously and the images of the little, ring, middle, and index fingers projected on shutters 96, 94, 92, and 90, respectively, are now recorded on zones 120, 122, 124, and 126, respectively. Now the chart 78 moves to the right until it touches sensor 82. At this time sensor 82 sends a signal so that chart 78 moves to the front until it touches sensor 84. Then this sensor sends a signal to illuminate selector key 42 turning off selector key 40.

Chart 78 is now on position B ready for the next recording. The person now positions the right thumb on lens 60. When the operator pushes selector key 42, shutter 108 opens and the image of the right thumb is recorded on zone 128 of the chart 78. Selector key 2 turns off and selector key 44 now illuminates. Then the person positions the four fingers of his right hand on lenses 62, 64, 66, and 68. At this time, the chart 78 is still on position B on chamber 30. When the operator pushes selector key 44, the shutters 106, 104, 102, and 100 open simultaneously and the images of the index, middle, ring, and little finger projected on shutters, 106, 104, 102, and 100, respectively, are now recorded on zones 130, 132, 134, and 136 of chart 78, respectively. Now chart 78 moves to the right until it touches sensor 86. At this time sensor 86 sends a signal so that chart 78 moves to the front until it touches sensor 88. This sensor sends a signal to illuminate selector key 46 turning off selector key 44. Now chart 78 is on position C ready for next recordings. The person positions the left thumb on lens 70 and the right thumb on lens 72. When the operator pushes selector key 46, shutters 116 and 114 open simultaneously and the images of the left and the right thumbs projected on shutters 116 and 114, respectively, are recorded on zones 138 and 140 of chart 78, respectively. Selector key 46 turns off and selector key 48 illuminates. Now the person positions the four fingers of the left hand on lens 74 and the four fingers of the right hand on lens 76. At this particular time chart 78 is still on position C on Chamber 30. When the operator pushes key 48, the shutters 112 and 110 open simultaneously and the images of the left four fingers and the right four fingers projected on shutters 112 and 110, respectively, are recorded on zones 142 and 144 of chart 78, respectively. At this time, chart 78 is released out of the system and is ready to be used, key 48 is turned off, another chart is fed on position A and key 38 is illuminated again. Now the apparatus is ready for the next person to be fingerprinted.

Referring to FIG. 5, the camera 20 may have approximately the same width as one third of the width of chart 78, and the same width as the shutter assembly 28. Also, the finger positioning assembly 36, the lens 24, the camera 20, and the shutter assembly 28 may be aligned on the same axis. The exterior enclosures of the apparatus must accommodate the film chamber 30.

In FIG. 6, a concave-convex lens is illustrated.

Figure 7:
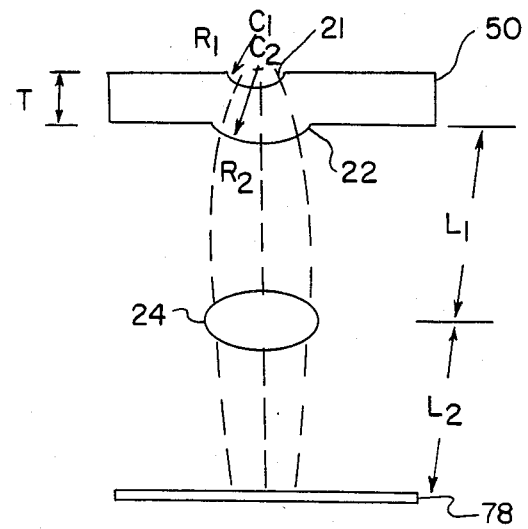
FIG. 7 is a diagramatic cross section of the concave-convex lens of the apparatus of FIG. 1.

With reference to FIG. 7, a lense 50 may be constructed to readily accommodate the shape of a person and provide a flat image for recording on film chart 78. The concave surface 21 of the lense 50 has been found to be effective if given a radius of between about one-half inch and about three-quarters of an inch, preferably about five-eighths of any inch. The thickness T of the lense may be selected primarily based on consideration of mechanical strength to avoid lense distortion from pressure of the finger being printed. The radius of the convex surface 22 may be selected in combination with the thickness T of the lense, the refractive index of the lense and the distance L1 to a lense 24 which focuses the image upon the film chart 78.

The convex surface 22 of the lense 50 has been found to be effective if given a radius of between about three-quarters of an inch and about one inch when the distances between the centers C1, C2 of curvature of the surfaces 21, 22 is about three-eighths of an inch.

Figure 8:
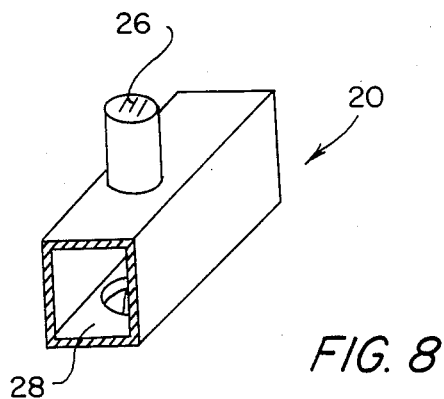
FIG. 8 is a fragmented perspective section of the camera of the apparatus of FIG. 1 showing the camera and shutter assembly.

In FIG. 8, the inside part of camera 20 is illustrated. The shutters assembly 28 constitutes the lower part of this camera. The entire camera 20 is attached to the film chamber 30.

Figure 9:
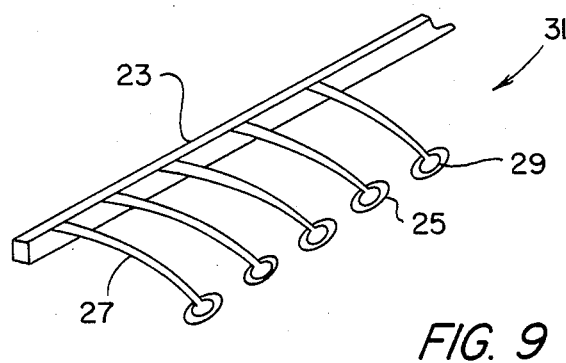
FIG. 9 is a schematic diagram of the lens cleaning assembly of the apparatus of FIG. 1.

A fingerprinted person who positions the fingers on a lens surface stains the same by impressing ridge marks on said surface. This affects the recording accuracy of the next fingerprinting operation. To prevent this problem, the finger positioning lenses are cleaned automatically after each fingerprinting operation. A cleaning assembly 31 attached to the apparatus is provided, as shown in FIG. 9. This assembly comprises a plurality of cleaning pads 25, one for each lens, a plurality of tension bars 27, each one connecting at pad 25 at one end, and a supporting bar 23 holding the other end of all bars 27 is a pivot joint 29. In this way, the pad 25 will adjust to the surface variations of the lenses to be cleaned. The assembly 31 also include means for urging the bar 23 toward the lenses and means for returning the bar 23 toward its original position. The lens cleaning operation may be performed automatically by the apparatus after chart 78 is released out of the apparatus.

It will thus be seen that the objects set forth above, and those made apparent by the preceeding description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed:
1. An apparatus for copying fingerprints, comprising:
   a first lens for converting a curved image to a flat image;
   a second lens aligned with said first lens to receive said flat image therefrom for transmitting said received image to a recording surface; and
   a shutter aligned with said transmitted image for selectively preventing said transmitted image from reaching said recording surface.
2. The apparatus of claim 1 wherein said first lens comprises a block of light transmissive material having a concave surface on one side of the block and a convex surface on another side of the block.
3. The apparatus of claim 2 wherein said concave surface is in the shape of a portion of a cylinder.
4. The apparatus of claim 3 wherein said convex surface is in the shape of a portion of a cylinder.
5. The apparatus of claim 4 wherein the cylindrical axis of said concave surface and the cylindrical axis of said convex surface are substantially coplanar.
6. The apparatus of claim 3 wherein the radius of said concave surface is in the range from about one-half inch to about three-quarters of an inch.
7. The apparatus of claim 4 wherein the radius of said convex surface is in the range from about three-quarters of an inch to about one inch.
8. The apparatus of claim 1 wherein said second lens is a double convex lens.
9. The apparatus of claim 1 wherein said first lens is a plano-concave lens.
10. The apparatus of claim 9 wherein the concave portion of said first lens is in the shape of a cylinder.
11. The apparatus of claim 9 wherein the radius of the concave portion of said first lens is in the range from about one-half inch to about three-quarters of an inch.
12. The apparatus of claim 1 further comprising plural first lenses for simultaneously converting a plurality of curved images to a like plurality of flat images.
13. The apparatus of claim 4 wherein the distance between the axis of said concave surface and the cylindrical axis of the convex surface is in the range from about one-quarter inch to about one-half inch.
14. The apparatus of claim 1 wherein said recording surface comprises a frame of photo sensitive film.
15. The apparatus of claim 14 wherein said film frame is generally planar and receives and records a plurality of images, each image being recorded in a predetermined zone of the film.
16. The apparatus of claim 3 wherein the arc of said concave surface is in the range from about 80 degress to about 100 degrees.
17. The apparatus of claim 4 where the arc of said convex surface is in the range from about 80 degrees to about 100 degrees.
18. A method for recording the image of a fingerprint of a person comprising the steps of:
   providing a shutter mechanism to selectively provide light access to a recording medium;
   converting the curved image of a fingerprint to a substantially flat image;
   transmitting the converted image to the shutter mechanism; and,
   selectively operating said shutter mechanism to permit said transmitted image to strike the recording medium.
19. The apparatus of claim 1 further comprising means to automatically clean one of the surfaces of said first lens.
20. The apparatus of claim 19 wherein said cleaning means comprises an actuating arm having a soft pad at one end thereof, said arm being based in a direction so as to apply pressure to the pad when the pad is moved across said one surface of said first lens.
21. A fingerprint recording device comprising:
   a plurality of first lenses, each first lens having a concave cylindrical surface for receiving a finger to be recorded and for transmitting an image of the ridges and depressions of the finger;
   a plurality of second lenses, each second lens being positioned to receive the transmitted image and being selectively operative to open and allow the transmitted image to pass therethrough;
   an image recording means to receive and record said transmitted image when one of the shutters is open;
   recording transport means to position said image recording means into alignment with each of said shutters such that the image recorded when the recording means is in alignment with each shutter does not substantially overlap the images recorded at the other shutters; and
   control means for indicating the readiness of the device for taking a new set of fingerprints; for signaling to an operator the recording of each of the images; and
   for sequencing the operation of the shutters in a predetermined order.

22. The device of claim 21 wherein said image recording means comprises a planar sheet of material onto which an image may be recorded.

23. The device of claim 21 wherein said image recording means comprises a sheet of photosensitive film.

24. The device of claim 22 further comprising means to automatically select one of a plurality of planar sheets at the start of a fingerprint process and to eject said one planar sheet from the device upon the completion of the fingerprint process.

25. The device of claim 22 wherein said planar sheet comprises a automatically developing photographic film.

26. The device of claim 21 wherein said first lens further comprises a convex cylindrical surface to receive said curved image and convert the curved image to a substantially flat image.

27. The device of claim 21 wherein said first lens is a concave-convex lens.

28. The device of claim 21 wherein said first lens is a plano-concave lens.

29. A fingerprint recording device comprising:

plural lens means, each lens means to transmit the image of a fingerprint to a recording plane;

plural shutter means intermediate of said lens means and said recording plane, each shutter means being selectively and independently operable to prevent an image from passing therethrough;

recording means positioned substantially in said recording plane for recording an image passing through a shutter means; and control means to operate said plural shutter means in a predetermined order to thereby record plural images on said recording means.

30. The device of claim 29 wherein said recording means includes a plurality of recording zones, each of said zones operable to record one of said images.

31. The device of claim 30 further comprising tranport means to selectively move said one of said recording zones of said recording means into alignment with each of said shutters.

32. The device of claim 31 wherein said lens means comprises a cylindrically symmetrical concave-convex lens.

* * * * *